United States Patent [19]
Reichert et al.

[11] Patent Number: 5,998,207
[45] Date of Patent: Dec. 7, 1999

[54] METHOD FOR TRANSFORMATION OF COTTON AND KENAF AND ORGANOGENIC REGENERATION

[75] Inventors: Nancy A. Reichert, Starkville, Miss.; Teong-Kwee Lim, Johor, Malaysia; Margaret M. Young, Starkville, Miss.

[73] Assignee: Mississippi State University, Mississippi State, Miss.

[21] Appl. No.: 09/096,360

[22] Filed: Jun. 12, 1998

Related U.S. Application Data

[60] Provisional application No. 60/049,963, Jun. 13, 1997.
[51] Int. Cl.$^6$ .............................. A01H 4/00; A01H 1/00; C12N 15/82; C12N 15/84
[52] U.S. Cl. ...................... 435/430; 435/430.1; 435/431; 435/469; 435/470; 800/293; 800/294; 800/298
[58] Field of Search ............................... 435/430, 430.01, 435/431, 469, 470; 800/294, 298, 293

[56] References Cited

PUBLICATIONS

Banks et al. Agrobacterium—mediated transformation of Kenaf (*Hibiscus cannabinus L.*) with the B–Glucuronidase (GUS) Gene. Plant Molecular Biology Reporter, vol. 11(2): 101–104, 1993.

MCLean et al. Callus induction and adventitious organogenesis of Kenaf (*Hibiscus cannabinus L*), Plant Cell Reports 11: 532–534, 1992.

*Primary Examiner*—David T. Fox
*Assistant Examiner*—Anne Marie Grünberg
*Attorney, Agent, or Firm*—Long Aldridge & Norman LLP; Steven B. Kelber

[57] ABSTRACT

Protocols for ogranogenic regeneration of cotton and kenaf are provided, which makes the in vitro regeneration of mature fertile plants in a reduced amount of time possible. Seedlings are the basis for monocotyl or hypocotyl explants which are transferred from the germination medium to a shoot initiation medium which comprises $AgNO_3$. These explants, prior to shoot initiation, may be transformed with exogenous DNA either through inoculation with a Agrobacterium agent such as *A. tumefaciens*, or through biolistic bombardment of the explants with microprojectiles having the exogenous DNA adsorbed onto their surface.

11 Claims, No Drawings

METHOD FOR TRANSFORMATION OF COTTON AND KENAF AND ORGANOGENIC REGENERATION

This application is a regular National application claiming priority from Provisional Application, U.S. application Ser. No. 60/049,963 filed Jun. 13, 1997. The entirety of the Provisional Application is incorporated herein by reference.

BACKGROUND OF THE INVENTION

This invention pertains to the transformation, on the one hand, and organogenic regeneration, on the other hand, of cotton plants and kenaf plants, both commercially important crops. While the overall system is applicable to both crops, which are members of the same family, cotton transformation and regeneration is discussed first, followed by kenaf regeneration. Both nuclear and plastid transformation are embraced.

Cotton

Cotton has been traditionally recalcitrant to regeneration in vitro. Most regeneration successes entailed the sole use of Coker lines which respond in tissue culture but are not agronomically important (Chlan et al., 1995; Firoozabady et al., 1987; Peeters et al., 1994; Shoemaker et al., 1986; Umbeck et al. 1987). Most (if not all) developed regeneration protocols entail the production of embryogenic callus from seedling explants such as cotyledon and hypocotyl sections, followed by the formation of somatic embryos with subsequent germination and conversion into mature cotton plants (Firoozabady and DeBoer, 1993; Firoozabady et al., 1987; Peeters et al., 1994; Rajasekaran et al., 1996; Shoemaker et al., 1986; Umbeck et al. 1987; U.S. Pat. Nos. 5,159,135, 5,244,802). This type of regeneration procedure could take up to 40 weeks and could produce unwanted mutations due to the presence of a prolonged callus phase prior to regeneration.

Cotton tissues have been successfully transformed with A. tumefaciens prior to generation of embryogenic callus used in regeneration (Firoozabady et al., 1987; Rajasekaran et al., 1996; Umbeck et al. 1987). Cotton has also been transformed via biolistics with tissues also undergoing regeneration via somatic embryogenesis (Rajasekaran et al., 1996). A few protocols have recently utilized intact meristem-tips as targets in biolistics-based transformations with regeneration occurring via a more direct organogenic route (Chlan et al., 1995; Finer and McMullen, 1990; McCabe and Martinelli, 1993). Although this has overcome some regeneration obstacles, it is technically demanding. Due to their extremely small size (<1.0 mm), the meristem-tips have to be excised with the aid of a dissecting microscope and once isolated, need to be utilized shortly thereafter.

Kenaf Kenaf (Hibiscus cannabinus L.), is a herbaceous annual fiber crop in the Malvaceae family. Since kenaf can be cultivated in a wide range of soils and climatic conditions, and requires only modest labor input, it is generally less expensive to produce when compared to most other fiber crops (Dempsey, 1975). Kenaf has been cultivated for use in various products, which include woven and non-woven textiles, newsprint, animal bedding, and potting soil mixes (Goforth and Fuller, 1994). Considerable interest has been shown for use of kenaf as a source of pulp for papermaking as newsprint made from kenaf is of high quality displaying high degree of smoothness and printability (Sij, 1987). The paper also has excellent ink-retention characteristics and its strength is well-suited to high speed newspaper presses.

Various pathogens adversely affect kenaf growth in the United States. Root-knot nematodes [Meloidogyne incognita (Kofoid and White) Chitwood] can contribute to yield losses up to 50% (Lawrence and McLean, 1991). In addition, Cristulariella moricola Hino (same as Cristulariella pyramidalis Waterman and Marshall) attacks kenaf leaves contributing to premature leaf abscission (Neely and Evers, 1976). In fact, this fungal pathogen has become a serious problem in the southern United States in recent years. The fungus causes a bull's-eye or zonate leafspot on both woody and annual plants, including 73 species in 36 families throughout the south central and south eastern United States. When kenaf was infected by the fungus, symptoms first appeared as necrotic lesions on leaves on the lower one-third of the plants (Neely and Evers, 1976). In 14 days, 50–75% of the leaves were found to be affected, at which time they usually abscised. By the time kenaf was ready for harvest, approximately 75% of the plant was defoliated (Neely and Evers, 1976). Cultivars from the following breeding series: Cubano, Everglades, Guatamela, and Tainung were all found to be susceptible to this fungal disease (B. S. Baldwin, personal communication).

Since all known kenaf cultivars are susceptible to C. moricola, there appeared to be little resistance available in the kenaf genome. Therefor, in vitro selection for resistant transformants would be an alternate way of establishing C. moricola resistant kenaf.

Accordingly, it remains an object of those of skill in the art to develop a method for regeneration of cotton and kenaf, in vitro, with an eye to obtaining genetic variation providing desirable qualities. In particular, it is a further object of those of skill in the art to obtain a method for transforming plant tissues with exogenous DNA, or obtaining mutation of endogenous DNA, and regenerating the tissues containing these DNA alterations and additions into mature, fertile plants.

SUMMARY OF THE INVENTION

The objects set forth above, and others, are obtained by the invention summarized below, and detailed on the following pages. Our regeneration method utilizes seedling explants such as hypocotyl and leaf explants as in the somatic embryogenic method, but regeneration is via organogenesis and does not involve the lengthy callus intermediate step. Regeneration therefore can be achieved in a shorter period of time and with a less likelihood of inducing unwanted mutations during the regeneration process. This organogenic regeneration protocol also has been demonstrated to work on commercially important cultivars and, therefore, would be more useful in transformation protocols. This regeneration method can be successfully combined with either type of transformation system, nuclear or plastid.

Seeds of commercial cultivars are surface disinfected and germinated aseptically on media. Seedling hypocotyl and cotyledon explants are placed on media (MS-based), Murashige and Skoog, 1962; NH-based, Nitsch and Nitsch, 1969) containing plant growth regulators (PGRs) 1-naphthaleneacetic acid (NAA) and thidiazuron (TDZ). Silver nitrate is also added to the media.

Approximately after four to six weeks in culture, small organogenic bumps appear. The organogenic bumps develop into viable shoots, then the shoots are excised for rooting.

For transformation, explants are placed on shoot initiation media prior to bombardment and/or incubated in A. tumefaciens bacterial cultures depending on the type of transformation desired. Tissues are then analyzed for the presence and integration of foreign DNA by various methods. Transgenic plants are regenerated via the above process on selective media. The subsequent progeny are also analyzed for patterns of foreign DNA inheritance.

DETAILED DESCRIPTION OF THE INVENTION

This invention pertains to methods of regeneration of both cotton and kenaf, using organogenesis, coupled with methods of transformation of these two important commercial crops, which can be used to introduce exogenous DNA to provide more desirable species, which can be regenerated using the regeneration protocols to provide mature, fertile plants which breed true (pass on the transformed or exogenous DNA and the traits encoded thereby). It is important that kenaf and cotton be treated similarly, since kenaf is slated for production in former cotton growing areas. In this respect, it should be noted that each kenaf seed is genetically unique. The inventors herein have germinated kenaf seeds, taken cuttings therefrom, and ultimately regenerated kenaf plants. For purposes of control and comparison, each line developed from a single seed is maintained separately, and referred to as a "seed clonal line" or SCL.

The detailed discussion below describes cotton regeneration, together with a method for transformation. Following that discussion, kenaf transformation is described. As noted briefly in the kenaf section, kenaf transformation is achieved according to the same general method as cotton transformation, described above. Additional experiments describing comparative conditions for kenaf regeneration follow the description.

It is important to note that both cotton and kenaf can be transformed using either Agrobacterium, such as *A. tumefaciens* coupled with wounding, or through biolistic bombardment. In connection with biolistic bombardment, both nuclear and plastid sources of exogenous DNA can be employed. Where using DNA for introduction into plastids, for transformation, smaller microprojectiles (0.4–0.7 microns verses 1.0–1.7 microns) may be advantageously employed, and DNA containing chimeric genes that can be expressed in plastids are utilized. One example, not intended to be limiting, of this type of vector is pZS197 containing a chimeric aadA gene which confers resistance to spectinomycin (Svab & Maliga, 1993). A similar plastid expression vector supplied by Dr. Henry Daniell, Auburn University was made available. Use of vectors containing the aadA gene enables the use of non-lethal selection to identify cells in plants containing transformed plastids. After bombardment, tissues would be grown on shoot initiation media containing spectinomycin but otherwise conducted as described herein below.

Transformation and Regeneration of Commercial Cotton and Kenaf Varieties

This method involves the following:

(1) surface sterilization and germination of seeds in vitro
(2) excision of tissues such as hypocotyl and leaf explants for use in transformation and regeneration
(3) introduction of DNA via *Agrobacterium tumefaciens* and/or biolistics
(4) selection of transformed tissues in the presence of antibiotic or herbicide to allow selective growth of transformed shoots (antibiotic or herbicide resistance gene is part of introduced DNA)
(5) growth of transformed shoots with subsequent rooting Detailed Protocols:
(1) Seeds[a] are surface disinfested in a bleach solution (25%, v/v) containing 0.5% SDS (detergent) for 20 min. then rinsed 4 times with sterile distilled water. Seeds are placed in/on Nitsch & Nitsch (NH-based) or Murashige & Skoog (MS-based) media (cefotaxime may be added) for 1–2 weeks to allow germination.

(2) Explants (hypocotyl and leaf sections) are excised and placed on shoot initiation media[b].

(3) DNA is introduced with *A. tumefaciens* via a modified protocol of those already reported. DNA was successfully delivered into cotton Coker lines (commercially unimportant) by Umbeck et al. 1987; hypocotyl sections), Firoozabady et al. (1987; cotyledon sections), and Rajasekaran et al. (1996; both explants)[c].

Introduction of DNA via the PDS-1000/He apparatus utilizes a modified protocol of those developed and currently used in N. Reichert's lab on other crops. Rajasekaran et al. (1996) successfully introduced DNA into embryogenic cotton lines (Coker and Acala) via the PDS-1000/He[d]. Multiple bombardments may increase transformation efficiencies, as has been demonstrated in cotton (Fajasekaran et al., 1996).

DNA introduction via a combination of biolistics and *A. tumefaciens* may also enhance the recovery of transformed cotton tissues. In other plant species this has been demonstrated to increase *A. tumefaciens* transformation efficiencies due to enhanced wounding (Bidney et al., 1992[e].)

(4) Selection systems currently in use include use of geneticin (G418) and kanamycin (chimeric nptII gene), phosphoinothricin (chimeric bar gene) and hygromycin (chimeric hph gene) for selection of transformants.

(5) Adventitious shoots emerge from tissues containing introduced DNA by growth on media containing a selection agent as discussed above. Transformed shoots that arise are cut and placed on a rooting medium which is a modification of the medium described by Chlan et al. (1995).

Notes:
a Commercial cotton varieties such as Deltapine 50, Stoneville 474 have been used.
b Modified shoot initiation media contain NAA, TDZ, and silver nitrate, One modification for cotton included the substitution of glucose for sucrose. In kenaf: NAA at 0.11 mg/l, TDZ at 0.2–3.5 mg/l, and silver nitrate at 0–50 mg/l induced adventitious shoots. In both cotton and kenaf, growth is under 16 hr photoperiod at approx. 24–27° C.
c Previously, researchers primarily introduced DNA into commercially unimportant lines, and regeneration (Coker and non-Coker lines) was through somatic embryogenesis which entailed a protracted culture period [up to 24 weeks to generate embryogenic callus (Rajasekaran et al., 1996]. This callus was then transferred to a second medium for production of somatic embryos, which were subsequently transferred to a third medium to achieve germination. Regeneration via adventive shoot organogenesis as described using modified kenaf media works on commercially important varieties and shorten the time it takes to produce transgenic cotton plants. In addition, since a prolonged callus phase will be avoided, there should be less chances for production of mutated cotton plants due to somaclonal variation.
d The tissues Rajasekaran et al. (1996) used in bombardments with the PDS-1000/He apparatus were embryogenic callus lines initiated from seedling explants. Regeneration then entailed development of somatic embryos from this callus (U.S. Pat. No. 5,244,802). As stated above, maintenance of cotton tissues in the callus phase for prolonged periods of time will increase the prevalence of mutations in cotton regenerants.
e Bidney, D., C. Scelonge, J. Martich, M. Burrus, L. Sims, and G. Huffmnan. 1992. Microprojectile bombardment of plant tissues increases transformation frequency by *Agrobacterium tumefaciens*. Plant Mol. Biol. 18:301–313.

Regeneration of Cotton

All culture stages are incubated under a 16 h photoperiod at room temp.

Seed Sterilization and Germination:

Cotton seeds (var. Deltapine 50) were soaked for five minutes in 70% ethanol, then surface sterilized for 25 minutes using 25% commercial bleach and 0.5% sodium dodecyl sulfate (SDS) on a shaker (200 rpm). The seeds were rinsed three times with sterile double distilled water and placed on a growth maintenance medium (GMS) GMSC (MS basal salts, 1.0 mg/l thiamine-HCL, 0.5 mg/l pyridoxine-HCL, 0.5 mg/l nicotinic acid, 100 mg/l myoinositol, 30 g/l glucose, 0.8 g/l phytagar, pH 5.8; plus 500 mg/l cefotaxime [for bacterial contamination]) for one week. (Liquid GMS/GMSC omits the phytagar). Germinated seeds (with at least the radicle emergent) were then placed in liquid GMSC (no phytagar) for an additional week. After one week in liquid medium, the cotyledons and shoot tips are clearly visible. Hypocotyl sections (one per seedling) are then excised with the acropetal cut made just below the cotyledonary nodes. The basipetal cut is made 10 mm below the initial cut.

Shoot Initiation, Elongation and Rooting:

Hypocotyl sections were placed horizontally on shoot initiation medium (GA2) which contained TDZ. Explants were maintained for six weeks on this medium. Shoot primordia were visible on the acropetal ends of hypocotyl sections after two weeks. After four and five weeks, leaves were clearly visible.

At the end of six weeks, the upper 5.0 mm portion of the acropetal ends were excised and placed on shoot elongation medium (GB) which contained BA. Cultures are maintained on this medium for an additional six weeks.

Shoots with a defined shoot pole are excised from shoot clumps for rooting. (Up to 5 shoots/explant have been generated, to date.) Shoots are placed on semi-solid GMS (medium above without cefotaxime). Roots appear within 6 weeks.

GA2: semi-solid GMS plus 0.35 mg/l TDZ, 0.1 mg/l NAA, and 10.2 mg/l silver nitrate
GB: semi-solid GMS plus 0.1 mg/l BA Variables Tested to Date Effect of Pre-Treatment:
Pre-treatment: GMSC or MSC (contains sucrose instead of glucose) for one week. Liquid GMSC, MSC or MST (MSC plus 0.35 mg/l TDZ) for an additional week.
Results: No shoot initiation of explants pre-treated with MST. Shoot initiation ranged from 12% (MSC→liquid GMSC) to 52% (GMSC→liquid GMSC).

Effect of Shoot Initiation Medium:
Shoot initiation media: GA2
   GA1 (contained sucrose, 0.35 mg/l TDZ, 0.1 mg/l NAA, and 10.2 mg/l silver nitrate)
Results: No shoot initiation on medium GA1. Up to 44% hypocotyl explants produced shoots on GA2.

Effect of Explant Orientation:
Orientation: Explant placed horizontal, basipetal end inserted or acropetal end inserted in the medium.
Results: No shoot regeneration was noted on explants placed with basipetal end in the medium. No significant differences, in regard to number of shoots produced, were observed between explants placed horizontally or those with acropetal end in the medium.

Effect of Photoperiod:
Photoperiod: Pre-treatment under continuous darkness or 16 h photoperiod. Shoot initiation under continuous darkness or 16 h photoperiod.
Results: Shoot regeneration was greater for explants under 16 h photoperiod (52%) than for those under continuous darkness (20%).

Effect of Elongation Medium:
Elongation media: MS (MSC without cefotaxime), GMS or GB (previous page)
Results: For those explants placed on MS, 100% death was observed. No shoot elongation was noted for those placed on GMS, although 10% of the explants produced roots. All explants placed on GB are still alive and have elongated. These explants have now been transferred to GC (GMS media±indole-3-butyric acid or IBA) (0.0–1.5 mg/l) for rooting.

Transformation of Cotton

Biolistics-Based Bombardments
40 explants (20/plate) were bombarded once with 720 μg M-10 microprojectiles, 1 μg DNA (pBI121) at 1350 psi with gap (¼ in) and target (7.5 cm) distances.
After incubation with X-glu, 50% of the explants displayed GUS-positive sectors. Of those responding, there was an average of 10 blue sectors per explant.

---

Seed germination for two weeks
[Surface sterilization then placement on GMSC for 1 week. Seedling transfer to liquid GMSC for 1 week]
↓
Shoot initiation on GA2 for 6 weeks
[Excised hypocotyl sections are placed horizontally on medium]
↓
Shoot elongation on GB for 6 weeks
↓
Root formation on GC for 6 weeks
↓
Acclimatization of plants for 2 weeks
Schematic diagram of shoot regeneration from hypocotyl sections of cotton.

---

Regeneration of Kenaf

Kenaf(*Hibiscus cannabinus* L.) is an annually renewable fiber source for the production of paper, carpet backing, broiler litter, bedding for horses, etc. It is characterized as having a short day, herbaceous , diploid (2n=2x=36), tropical origin, primarily self-pollinated. It has exhibited limited genetic variability amongst cultivars grown in Southeast USA. Kenaf is related to cotton (Gossypium sp.) and shares similar agronomic and climatic requirements. Like the other members of this family, kenaf can be adversely affected by pests, weeds and diseases. Kenaf is slated for production in former cotton growing areas. Thus, resistance strategies developed for cotton will need to be incorporated into kenaf breeding programs. The improvement of kenaf through transformation coupled with organogenic regeneration employs several art recognized protocols outlined below.

*Agrobacteriun Tumefaciens* (A.t.)
   plant pathogenic soil bacterium which primarily infects wounded dicots and gymnosperms
   disarmed A.t. strains are used routinely for plant transformations
   mediates the production of transgenic plants
   used to produce transgenic cotton Biolistic Transformation
   introduction of DNA via direct transfer techniques
   successfully used to transform a wide range of crops including dicots and monocots
   used to target cells within tissues or organs that have high morphogenic potential
   more genotype-independent when compared to A.t. infection

MATERIALS AND METHODS

Maintenance of Seed Clonal Lines (SCL)
   kenaf seeds were surface sterilized for 25 minutes in a solution containing 25% (v/v) commercial bleach and 0.5% (w/v) SDS then placed on MSO medium MSO had MS (Murashige and Skoog, 1962) basal salts and vitamins, sucrose and agar, pH 5.8 incubated in growth chamber under 16 h photoperiod at 25±2° C.

after germination, plants were subcultured every 3–4 weeks via shoot tips and nodal sections plants from each seed were maintained independently as SCL due to genetic distinctness of each seed SCL of cultivars Everglades 41 (E41), E71, Cubano, Tainung 2 (Tai2) and Guatemala 45 (G45) were maintained Dose Response Studies leaf explants (5×5 mm) of three SCL of E41 and one SCL Tai2 were either bombarded with tungsten alone or placed directly on shoot initiation medium (MSO plus 0.1 mg/l NAA, 0.35 mg/l TDZ and 10.2 mg/l AgNO$_3$) with different concentrations of kanamycin and geneticin experiment consisted of 5 explants/plate and 3 replications/treatment explants were observed after 2 weeks and 1 month and the minimum inhibitory concentration (MIC) determined Agrobacterium-Mediated Transformation four different plasmid constructs utilized constructs based on modified pMON316 which contained chimeric neomycin phosphotransferase II (NPTII) gene, nopaline synthase (NOS) promoter and 3' end designated as NOS/NPTII/NOS; and cauliflower mosaic virus 35S promoter (35S) and NOS 3' separated by a multilinker region modified pMON316 constructs were cointegrated into A.t. harboring pGV3850 which contained T-DNA LB and RB with pBR322 sequences in-between, and vir genes constructs also contained β-glucuronidase (GUS) coding sequence; upstream sequences included 35S, double 35S (enhanced; D35S), and an alfalfa mosaic virus (AMV) translational enhancer

141: 35S/AMV/GUS/NOS
142: 35S/GUS/NOS
176: D35S/AMV/GUS/NOS
177: D35S/GUS/NOS
negative control: -/GUS/NOS bacterial strains were recovered from frozen stocks stored at −80° C. in glycerol, were cultured in the dark at 28±° C. for 2 days on LB medium with agar and appropriate antibiotics single colonies were then grown overnight in liquid LB with appropriate antibiotics at 28±° C. on a gyrator shaker at 200 rpm, until a final density of A$_{600}$=0.6–0.8 aseptic kenaf leaf explants (trimmed to 5×5 mm) were precultured for varying numbers of days (0–3 days; additional wounding or not), then placed into A.t. culture (1–10 minutes; with or without acetosyringone)

explants were blotted dry on sterile filter paper and placed on coculture medium (shoot initiation; with or without acetosyringone) under 16 h photoperiod for 2 days at 25±2° C.

shoot initiation medium consisted of MSO with NAA, TDZ and AgNO$_3$ 8 explants/plate with 3 replications/treatment; each experiment was repeated at least twice explants were transferred to selection medium (shoot initiation medium containing 500 mg/l cefotaxime plus selective antibiotic at the MIC concentration)

parameters investigated were leaf preculture times of 0, 1, 2, 3 minutes and inoculation times of 1, 5 and 10 minutes presence/absence of 20 μM acetosyringone in overnignt A.t. culture and 100 μM AS in coculture medium using the four plasmid constructs additional wounding prior to A.t. inoculation by delivering tungsten into the leaf explants optimized parameters were used to transform three SCL of five cultivars transfers were made to selection medium every month putative transformants were placed on rooting medium (MSO plus 500 mg/l cefotaxime and 5 mg/l geneticin)

controls included uninoculated leaf explants

Biolistic-Mediated Transformation twenty four aseptic leaf explants (trimmed to 5×5 mm) were placed in the center 1 cm area of each petri plate plasmid DNA (pBI121; NOS\NPTII\NOS-35S\GUS\NOS) was precipitated unto tungsten microprojectiles biolistic particle delivery system (model PDS-1000/He) was used to deliver DNA explants were placed on selection medium 3 days post-bombardment with transfers made every month to new selection medium controls were explants bombarded with tunsgsten alone and bombarded with pBI101.2 (NOS\NPTII\NOS—GUS\NOS)

parameters investigated were
pressure (650, 900, 1100 psi)
gap distance (⅛, ¼, ⅜ inches)
target distance (7.5, 9.0, 11.0 cm)
tungsten size (0.7 , 1.11, 1.73 μm)
number of bombardments (1, 2, 3 shots)
amount of DNA (1, 2, 3 μg/μl)
preculture times (0, 1, 2, 3, 7 days)

optimized parameters were used to transform three SCL of five cultivars

For All leaf explants were assayed histochemically for the presence of GUS activity as described by Jefferson (1987), after 9 days for A.t. -mediated; and after 3 days for biolistic transformation if the blue color was obscured, explants were bleached by incubation in (3:1) absolute ethanol:acetic acid transformation efficiency was determined by:
the number of explants producing GUS-positive sectors

RESULTS

Dose Response Studies kanamycin at concentrations from 0–160 mg/l did not inhibit explant expansion or callus growth after 2 weeks or 1 month geneticin at a concentration of 10 mg/l (MIC) totally disrupted growth after 2 weeks for E41. For Tai2, the MIC was determined to be 15 mg/l no differences in MIC observed between explants bombarded or unbombarded for E41 and also Tai2

10 or 15 mg/l geneticin was added to the selection medium

Agrobacterium-Mediated Transformation (FIG. 1)

optimized parameters
leaf preculture for 2 days
inoculation with A.t. for 10 minutes coculture for 2 days prior to selection
  the presence of 20 μM acetosyringone (AS) in bacterial and 100 μM AS in coculture media could enhance transformation efficiencies. Plasmid construct #177 performed the best in terms of GUS-positive areas.
  enhanced wounding prior to inoculation with A.t. decreased transformation efficiencies
significant differences were noted amongst cultivars for the prevalence of GUS-positive sectors (Table 1)
cultivars G45, E41 and Tai2 yielded similar GUS-positive areas as did some SCL in Cubano and E71
within each cultivar, significant differences between SCL were noted for Cubano and E71, reinforcing the need to use SCL when working with kenaf Biolistic-Mediated Transformation
  optimized parameters
    pressure of 900 psi
    gap distance of ¼ inch
    target distance of 7.5 cm
    tungsten size of 0.7 μm
    2 μg\μl DNA delivered in one shot
    preculture time of 7 days
  significant differences were noted in transient expression of GUS within cultivars (Table 2)
  only cultivar E41 yielded similar numbers of GUS-positive spots within the SCL
  within cultivars, Tai2 showed greatest range of GUS-positive spots
Generation of Transgenic Kenaf Plants
  after inoculation with A.t. and bombardment, explants have been maintained on selection medium
  regenerated shoots have been generated on A.t. inoculated and bombarded leaf explants maintained on selection media
  putative transformed shoots from A.t. inoculation have rooted on selection medium

DISCUSSION

GUS expression assay demonstrated the effective transformation of kenaf with exogenous DNA whether introduced by inoculation with transformed A.t. or by biolistic bombardment. Nuclear or plasmid DNA can be employed. Subsequent regeneration of kenaf transformants, discussed in detail below, resulted in in vitro regeneration of transformants. This has been confirmed using PCR analysis to demonstrate the positive incorporation in transformants of the NPTII gene. Importantly, PCR has demonstrated effective transformation using both A.t. inoculation and biolistic bombardment. Clearly, the two methods can be combined to further enhance recovery of transformants.

TABLE 1

The effect of SCL and cultivar on
prevalence of GUS-positive sectors in A.t.
inoculated leaf explants.

| Cultivar (mm$^2$) | SCL | Mean GU$^y$Spositive area per explant |
|---|---|---|
| Cubano | 3 | 10.26 b |
|  | 4 | 11.30 b |
|  | 5 | 17.75 a |
| G45 | 1 | 18.80 a |
|  | 7 | 17.40 a |
|  | 11 | 16.35 a |

TABLE 1-continued

The effect of SCL and cultivar on
prevalence of GUS-positive sectors in A.t.
inoculated leaf explants.

| Cultivar (mm$^2$) | SCL | Mean GU$^y$Spositive area per explant |
|---|---|---|
| E41 | 2 | 17.40 a |
|  | 4 | 17.75 a |
|  | 5 | 18.45 a |
| E71 | 1 | 12.34 b |
|  | 2 | 13.21 b |
|  | 9 | 17.05 a |
| Tai2 | 1 | 16.00 a |
|  | 2 | 15.31 a |
|  | 4 | 16.36 a |

Eight leaf explants were placed per plate, with three replicate plates per variable tested. Leaf explants were precultured for 2 days, inoculated in bacterial culture (20 μM AS) containing construct #177 for 10 minutes and cocultured (100 μM AS) for 2 days. The experiment was repeated twice and numbers presented are averages of both experiments.
Mean separation in column by LSD, p <0.05. Means followed by the same letter are not significantly different.
$^z$= seed clonal line; number related to original seedling number
$^y$= β-glucuronidase; activity assayed histochemically according to Jefferson (1987), after 7 days on selection medium; leaf explants were 5 × 5 mm in size (25 mm$^2$)

TABLE 2

The effect of SCL and cultivar on
prevalence of GUS-positive spots in bombarded
leaf explants

| Cultivar | SCL$^z$ | Mean GU$^y$S-positive spots per explant |
|---|---|---|
| Cubano | 3 | 3.1 e |
|  | 4 | 7.8 b–e |
|  | 5 | 10.0 a–d |
| G45 | 1 | 4.4 c–e |
|  | 7 | 4.2 de |
|  | 11 | 10.6 a–c |
| E41 | 2 | 11.2 ab |
|  | 4 | 11.0 ab |
|  | 5 | 11.2 ab |
| E71 | 1 | 10.6 a–c |
|  | 2 | 4.5 c–e |
|  | 9 | 8.6 a–e |
| Tai2 | 1 | 14.3 a |
|  | 2 | 12.9 ab |
|  | 4 | 2.6 e |

Twenty four leaf explants were precultured for 7 days and then bombarded with 2 μg\μl of the plasmid pBI121. The experiment was repeated twice and numbers presented are averages of both experiments. Mean separation in colum by LSD, p < 0.05. Means followed by the same letter are not significantly different.
$^z$= seed clonal line; number related to original seedling number
$^y$= β-glucuronidase; activity assayed histochemically according to Jefferson (1987), 3 days post-bombardment; leaf explants were 5 × 5 mm in size (25 mm$^2$)
Precultured leaf explants (trimmed to 5 × 5 mm)
[2 days for Agrobacterium and 7 days for biolistics]

Precultured Leaf Explants (Trimmed to 3.5 mm)
(2 days for Agrobacterium or 7 days for biolistics)
↓
Inoculation with Agrobacterium (for 10 minutes)
or delivery of DNA by bombardment
↓
Placement on coculture medium for
2 days then onto selection medium for Agrobacterium
or placement on selection 3 days post-bombardment
↓

-continued

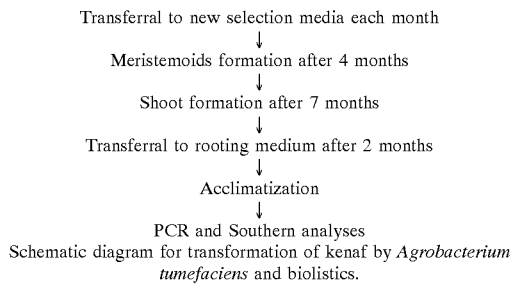

Transferral to new selection media each month
↓
Meristemoids formation after 4 months
↓
Shoot formation after 7 months
↓
Transferral to rooting medium after 2 months
↓
Acclimatization
↓
PCR and Southern analyses Schematic diagram for transformation of kenaf by *Agrobacterium tumefaciens* and biolistics.

Kenaf Regeneration Studies

Seed Germinations

Kenaf seeds were obtained from cold storage located at the Plant Science Research Center (North farm), Mississippi State University. Seeds were wrapped in four layers of cheesecloth, immersed in 75% ethanol for three minutes, then surfaced sterilized in a 25% solution of commercial bleach plus 0.5% sodium dodecyl sulphate (SDS) for 25 minutes. After five sterile water rinses, the seeds were placed in MS-0 medium [MS salts, vitamins (100 mg/l myo-inositol, 0.5 mg/l nicotinic acid, 0.5 mg/l pyridoxine-HCl, 1.0 mg/l thiamine-HCl) 3% (w/v) sucrose, 0.8% phytagar, no PGRs] for germination.

Explant Choice, Clonal Line Multiplication and Maintenance

Young leaves from seed clonal lines were used in all adventitious regeneration experiments and some were used in evaluating resistance to Cristulariella in vitro. Young leaves were excised from the seed clonal lines and trimmed on the edge, then cut into 5 mm$^2$, and used in experiments. Aseptically germinated kenaf seeds were maintained and multiplied by nodal cuttings in Magenta boxes containing MS-0. Multiplications of seed clonal lines were made every four to six weeks to have sufficient young leaves.

Plant Growth Regulators Preparation and Storage

Plant growth regulators (PGRs) were prepared by dissolving in appropriate solvent, and filter-sterilized with 0.2 µM filter, then stored in appropriate temperature (4° or −20° C.). TDZ was dissolved in dimethylsulfoxide (DMSO) and stored at 4° C.

Culture Conditions

Unless specifying, all explants were cultured in 25×100 mm petri dishes, five explants per plate under culture conditions: 25°/21° C. day/night temperatures, 16 hours photoperiod, and light intensity of 52 µEmn$^{-2}$s$^{-1}$.

Adventitious Shoot Regeneration

Experiment 1

Results from initial experiment showed kenaf cultured in lower concentration of TDZ with NH based medium were able to produce shoots. The objective of this experiment was to compare the responses of kenaf explants in NH based medium and TN12 medium (Liu, 1993). TDZ was added to NH based medium at 2.2 or 3.0 mg/l (designated as NH10 or NH11) plus 0.1 mg/l NAA and 30 g/l sucrose. Leaf sections from seed clonal lines of five cultivars: C108, E41, E71, G45 and G48, were used in the experiment. Each cultivar composed of seven seed clonal lines, with each clonal line served as one replication. Observations were taken every four weeks until end of experiment, which was twelve weeks after culture.

Experiment 2

Many reports on TDZ for adventitious shoot regeneration utilized MS salts in combination with B5 vitamins. The objective of this experiment was to determine the effect of MS salts in combination with B5 vitamins on the adventitious regeneration of kenaf. Also, ten kenaf cultivars were tested to determine which medium was the best media for adventitious regeneration. The cultivars tested were: C108, Cubano, E41, E71, G45, G48, India, Tainung 1, Tainung 2, and SF459. Similar to previous experiment, leaf sections from seven seed clonal lines of each cultivar were tested in three media with three replications per treatments.

Experiment 3

Silver nitrate were incorporated into NH10 medium at four concentrations: 5, 10, 20 and 50 mg/l. The medium also contained 30 g/l sucrose or glucose plus 2.2 mg/l TDZ and 0.1 mg/l NAA. Leaf section from E41S5 and G45S4 were used to investigate the effect of silver nitrate for the adventitious shoots regeneration of kenaf. Observations were taken at four week intervals for a period of 12 weeks. cl

Experiment 4

Four seed clonal lines: C108S2, C108S3, E41S7, and G48S5 were tested on NH10 medium plus 20 mg/l silver nitrate. NH10 medium was used to compare the number of shoots regenerated from each cultivar. Five leaf explants were placed per petri dish, three replications per treatments.

Experiment 5

The effects of silver nitrate on TN12 medium for regeneration were evaluated in this experiment. AgNO$_3$ at 5, 10, 20 and 50 mg/l were added to TN12 medium, and leaf explants of TailS1 and E71S3 were placed on the medium for regeneration. Number of shoots regenerated from each medium were counted and compared to determine which concentration of silver nitrate worked the best with TN12 medium.

Experiment 6

From the first four experiments, it was observed that most of the adventitious shoots regenerated were from the mid vein area, specifically on the leaf base region. To confirm this, leaf sections from two seed clonal lines E41S5 and G48S6 were used for experiment. The leaves were trimmed on edges, split through the midrib into half, then further cut into four pieces. Explants from each position were placed in separate petri dishes containing NH10 medium, with three replications for each positions.

The results of the above studies uniformally demonstrated the efficacy of the organogenic regeneration of kenaf according to the inventive protocol.

Bibliography

1. Ahloowalia, B. S. 1986. Limitations to the use of somaclonal variation in crop improvement. Adv. Agric. Biotechnol. 14–27.
2. Baird, R. E. 1995. First report of *Cristulariella moricola* on kenaf in Georgia. Plant Dis. 79:425.
3. Bateman, D. F., and S. V. Beer. 1965. Simultaneous production and synergistic action of oxalic acid and polygalacturonase during pathogenesis by *Sclerotium rolfsii*. Phytopathology 55:204–211.
4. Blackmon, W. J., and B. D. Reynolds. 1982. In vitro shoot regeneration of *Hibiscus acetosella*, muskmelon, watermelon, and winged bean. HortScience 17:588–589.

5. Blake, J. H., J. D. Mueller, and S. A. Lewis. 1994. Disease of kenaf in South Carolina. Plant Dis. 78:102.
6. Chandler, S. F., and T. A. Thorpe. 1986. Variability from plant tissue cultures: biotechnological application to improving salinity tolerance. Biotech. Adv. 4:117–135.
7. Chi, G., D. G. Barfield, G. Sim, and E. Pua. 1990. Effect of $AgNO_3$ and aminoethoxyvinvylglycine on in vitro shoot and root organogenesis from seedling explants of recalcitrant Brassica genotypes. Plant Cell Rpt. 9:195–198.
8. Cline, M. N., and D. Neely. 1979. *Cristulariella pyramidalis* and its pathogenesis on black walnut. Plant Dis. Rpt. 63:1028–1932.
9. Cline, M. N., J. L. Crane, and S. D. Cline. 1983. The teleomorph of *Cristulariella moricola*. Mycol. 75:988–994.
10. Cook, C. G. 1993. Evaluation of ten kenaf cultivars for resistance to field infection by *Macrophomina phaseolina*. Ind. Crops and Prod. 2:23–25.
11. Dempsey, J. M. 1975. Fiber Crops. Rose Printing Company, Tallahassee, Fla., pp. 203–304.
12. Dixon, R. A. 1985. Isolation and maintenance of callus and cell suspension cultures. In Plant Cell Culture: A Practical Approach, R. A. Dixon, ed., IRL Press, Washington, D.C., pp. 1–20.
13. Evans, D. A. 1989. Somaclonal variation-genetic basis and breeding applications. Trends Genet. 5:46–50.
14. Evenor, D., E. Pressman, Y. Ben-Yephet, and L. Rappaport. 1994. Somaclonal variation in celery and selection by co-culturing toward resistance to *Septoria apicola*. Plant Cell Tissue Organ Cult. 39:203–210.
15. Favaront, F., P. Alghisi, P. Marciano, and P. Magro. 1988. Polygalacturonase isoenzymes and oxalic acid produced by *Sclerotinia sclerotiorum* in soybean hypocotyls as elicitor of glyceollin. Physiol. Mol. Plant Pathol. 33:385–395.
16. Firoozabady, E., and D. L. DeBoer. 1993. Plant regeneration via somatic embryogenesis in many cultivars of cotton (*Gossypium hirsutum L.*). In Vitro Cell. Dev. Biol. 29P:166–173.
17. Goforth, C. E. and M. J. Fuller. A summary of kenaf production and product development research 1989–1993. Miss. Agric. Forest. Expt. Stn. Bull. 1101.
18. Gonzales, R. A., and J. M. Widholm. 1985. Selection of plant cells for desirable characteristics: inhibitor resistance. In Plant Cell Culture: A Practical Approach, R. A. Dixon, ed., IRL Pres, Washington, D.C., pp. 67–68.
19. Grand, L. F. 1978. New hosts of *Cristulariella pyramidalis* in North Carolina. Plant dis. Rpt. 62:841–842.
20. Grand, L. F., and J. A. Menge. 1974. Sclerotia of *Cristulariella pyramidalis* in nature. Mycologia 66:712–715.
21. Hammerschlag, F. A. 1990. Resistance responses of plants regenerated from peach callus cultures to *Xanthomonas campestris* cv. Pruni. J. Amer. Soc. Hort. Sci. 115:1034–1037.
22. Hyde, C. L., and G. C. Phillips. 1996. Silver nitrate promotes shoot development and plant regeneration of chile pepper (*Capsicum annuum L.*) Via organogenesis. In Vitro Cell. Dev. Biol. 32P:72–78.
23. Ibrahim, K. M., J. C. Collins, and H. A. Collins. 1990. Characterization of progeny of *Coleus blumei* following an in vitro selection for salt tolerance. Plant Cell Tissue Organ. Cult. 28:139–145.
24. Kurian, P., and D. A. Stelzig. 1979a. Growth and oxalic acid production by *Cristulariella pyramidalis* on selected culture media. Phytopathology 69:712–714.
25. Kurian, P., and D. A. Stelzig. 1979b. The synergistic role of oxalic acid and endogalacturonase in bean leaves infected by *Cristulariella pyramidalis*. Phytopathology 69:1301–1304.
26. Kurian, P., D. A. Stelzig, J. F. Baniecki, and M. Marshall. 1977. Toxin production by *Cristulariella pyramidalis*. Mycologia 69:1203–1206.
27. Larkin, P. J., P. M. Banks, R. Bhati, R. I. S. Brettell, P. A. Davies, S. A. Ryan, W. R. Scowcroft, L. H. Spindler, and G. J. Tanner. 1989. From somatic variation to variant plants: mechanisms and applications. Genome 31:705–711.
28. Larkin, P. J., and W. R. Scowcroft. 1981. Somaclonal variation-a novel source of variability from cell cultures for plant improvement. Theor. Appl. Genet. 60:197–214.
29. Latham, A. J. 1987. Laboratory and greenhouse techniques for evaluating selected fungicides against *Cristulariella moricola* on pecan leaves. Plant Dis. 71:1010–1014.
30. Lawrence, G. W., and K. S. McLean. 1991. Reproductive potential of plant parasitic nematodes on kenaf. Miss. Agric. Forest. Expt. Stn. Res. Rpt. 16, No. 2.
31. Lepoivre, P., J. Visuer, K. Duhem, and N. Carels. 1986. Double-layer culture techniques as a tool for the selection of calluses resistant to toxic material from plant pathogenic fungi. Somaclonal Variations and Crop Improvement. Martin Nijhoff. Hingham, Mass., USA, pp:45–52.
32. Littrell, R. H., and P. F. Bertrand. 1981. Management of pecan fruit and foliar diseases with fungicides. Plant dis. 65:769–774.
33. Liu, D. L. 1994. Protoplast isolation, fusion, and in vitro regeneration of kenaf (*Hibiscus cannabinus L.*), Masters thesis. Mississippi State University. 130 pp.
34. Litz, R. E. 1986. Germplasm modification and its potential for finding new sources of resistance to diseases. J. Nematol. 18:18–22.
35. Ludwig, A. C., J. F. Hubstenberger, and G. C. Phillips. 1992. Screening of Allium tester lines in vitro with *Pyrenochaeta terrestris* filtrates. HortScience 27:166–168.
36. Marciano, P., P. Di Lenna, and P. Magro. 1983. Oxalic acid, cell wall-degrading enzymes and pH in pathogenesis and their significance in the virulence of two *Sclerotinia sclerotiorum* isolates on sunflower. Physiol. Plant Pathol. 22:339–345.
37. McLean, K. S., G. W. Lawrence, and N. A. Reichert. 1992. Callus induction and adventitious organogenesis of kenaf (*Hibiscus cannabinus L.*). Plant Cell Rpt. 11:532–534.
38. Murashige, T., and F. Skoog. 1962. A revised medium for rapid growth and bioassay with tobacco tissue culture. Physiol. Plant. 15:473–497.
39. Msikita, W., H. T. Wilkinson, and R. M. Skirvin. 1990. Resistance of in vitro-derived cucumber plants to *Pythium aphanidermatum*. HortScience 25:967–969.
40. Neely, D., and r. A. Evers. 1976. New host records for *Cristulariella pyramidalis*. Plant dis. Rpt. 60:590–593.
41. Niedbalski, M., J. L. Crane, and D. Neely. 1979. Illinois fungi 10. Development, morphology, and taxonomy of *Cristulariella pyramidalis*. Mycolologia 71:722–730.
42. Nitsch, J. P., and C. Nitsch. 1969. Haploid plants from pollen grains. Science. 16:85–87.
43. Phillips, R. L., S. M. Kaepler, and P. Olhoft. 1994. Genetic instability of plant tissue cultures: breakdown of normal controls. Proc. Natl. Acad. Sci. USA. 91:5222–5230.
44. Pollack, F. G., and H. E. Waterworth. 1969. A leaf spot disease of kenaf in Maryland associated with *Cristulariella pyramidalis*. Plant Dis. Rpt. 53:810–811.

45. Pua, E., G. Sim, G. Chi, and L. Kong. 1996. Synergistic effect of ethylene inhibitors and putrescine on shoot regeneration from hypocotyl explants of Chinese radish (*Raphanus sativus L.* var. Longipinnatus Bailey) in vitro. Plant Cell Rpt. 15:685–690.
46. Purnhauser, L., P. Medgyesy, M. Czako, P. J. Dix, and L. Marton. 1987.
Stimulation of shoot regeneration in *Triticum aestivum* and *Nicotiana plumbaginifolia* Viv. Tissue cultures using the ethylene inhibitor $AgNO_3$. Plant Cell Rpt. 6:1–4.
47. Redhead, S. A. 1975. The genus Cristulariella. Can. J. Bot. 53:700–707.
48. Redhead, S. A. 1979. Mycological observations: 1, on Cristulariella; 2, on Valdensinia; 3, on Neolecta. Mycologia 71:1248–1253.
49. Reichert, N. A., and B. S. Baldwin. 1995. Potential for kenaf improvement via somaclonal variation. Proc. Intl. Kenaf Assoc. Conf. 7:107–112.
50. Reichert, N. A., and D. Liu. 1994. Protoplast culture and in vitro regeneration of kenaf. Proc. Intl. Kenaf Assoc. Conf. 6:61–65.
51. Reichert, N. A., and D. Liu. 1996. Protoplast isolation culture, and fusion of kenaf (*Hibiscus cannabinus L.*). Plant Cell Tissue Organ. Cult. 44:201–210.
52. Reynolds, B. D., and W. J. Blackmon. 1983. Embryogenesis and plantlet regeneration from callus of *Hibiscus acetosella*. J. Amer. Soc. Hort. Sci. 108:307–310.
53. Rowe, D. E. 1993. Oxalic acid effects in exudates of *Sclerotinia trifoliorum* and *S. sclerotium* and potential use in selection. Crop Sci. 33:1146–1149.
54. Shepard, J. F. 1981. Protoplasts as sources of disease resistance in plants. Ann. Rev. Phytopathology 19:145–166.
55. Sij, J. W. 1987. Kenaf production in southeast Texas. Texas Agric. Exp. Stn. Prog. Rpt. 4536.
56. Tomaso-Peterson, M., and J. V. Krans. 1990. Evaluation of a new in vitro cell selection technique. Crop Sci. 30:226–229.
57. Trolinger, J. C., E. S. Elliot, and R. J. Young. 1978. Host range of *Cristulariella pyramidalis*. Plant Dis. Rpt. 62:710–714.
58. Viseur, J. 1990. Evaluation of fire blight resistance of somaclonal variants obtained from the pear cultivar 'Durondeau'. Acta Hort. 273:275–284.
59. Waterman, A. M., and R. P. Marshall. 1947. A new species of Cristulariella associated with leaf spot of maple. Mycologia 39:690–698.
60. Jefferson, R. A., Assaying Chimeric Genes in Plants: the GUS gene fusion system. Plant, Mol. Biol. Rptr. 5:387–405 (1987).

This invention has been described generically, and by reference to specific examples. Variations on the example parameters, particularly concentration and identity of media contents, time distance, and size, will occur to those of skill in the art without the exercise of inventive faculty. These variations remain within the scope of the invention unless excluded by the recitations of the claims below.

What is claimed is:

1. A method of regenerating, in vitro, a mature fertile kenaf plant through direct organogenesis, said method comprising:

excising a first explant, which is a leaf explant, maintaining said first explant on a shoot initiation medium comprising thidiazuron until shoot formation on said first explant is observed, transferring said shoot-bearing first explant to a growth maintenance medium until root formation is observed indicating formation of a rooted plantlet, and planting said rooted plantlet and growing the same into a mature plant.

2. The method of claim 1, wherein said leaf explant is obtained from a seedling which is obtained by sterilization of seeds of kenaf and placing said sterilized seeds on a NH or MS growth medium comprising a plant growth regulator selected from the group consisting of a cytokinin or an auxin or a mixture thereof.

3. The method of claim 2, wherein said cytokinin is thidiazuron (TDZ) and said auxin is 1-naphthaleneacetic acid (NAA).

4. The method of claim 1, wherein said shoot initiation medium comprises $AgNO_3$ in an amount up to 250 mg/l.

5. The method of claim 4, wherein said shoot initiation medium further comprises NAA.

6. A method of regenerating, in vitro, a mature kenaf plant through direct organogenesis, comprising excising leaf explant from seedlings germinated from 5–15 days on a germination medium, maintaining said explant on a shoot initiation medium comprising thidiazuron with its basipetal end until at least one of leaf formation or rudimentary shoot formation on said first explant is observed, excising an acropetal portion from said explant and maintaining said acropetal portion on said shoot initiation medium until shoots are formed, transferring said shoots to a growth maintenance medium until roots appear, indicating the formation of a rooted plantlet, and planting said rooted plantlet in a growth supporting medium and growing said plantlet into a mature plant.

7. A method of obtaining a kenaf plant expressing exogenous DNA, comprising:

germinating a sterilized seed of kenaf for a period of 5–10 days to produce a seedling, after which a leaf explant is obtained from said seedling, introducing exogenous DNA into said explant by at least one of a) inoculating said explant with *A. tumefaciens* which carries said exogenous DNA or b) bombarding said explant with microprojectiles of tungsten or gold bearing on the surface thereof said exogenous DNA, maintaining said explant on a shoot initiation medium comprising thidiazuron until shoot formation through direct organogenesis on said explant is observed, transferring said shoot-bearing explant to a growth maintenance medium until root formation is observed indicating formation of a rooted plantlet, and planting said rooted plantlet and growing the same into a mature plant, wherein said plant expresses said exogenous DNA.

8. The method of claim 7, wherein said seedling is obtained by sterilization of seeds of cotton or kenaf and placing said sterilized seeds on a NH or MS growth medium.

9. The method of claim 7, wherein said shoot initiation medium comprises $AgNO_3$ in an amount up to 250 mg/l.

10. The method of claim 8, wherein said shoot initiation medium further comprises an auxin.

11. The method of claim 10, wherein said auxin is NAA.

* * * * *